(12) United States Patent
Muhlsteff

(10) Patent No.: US 10,959,658 B2
(45) Date of Patent: Mar. 30, 2021

(54) METHOD AND DEVICE FOR IDENTIFYING A SUBJECT IN A SENSOR BASED MONITORING SYSTEM

(75) Inventor: Jens Muhlsteff, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 370 days.

(21) Appl. No.: 13/821,080

(22) PCT Filed: Sep. 16, 2011

(86) PCT No.: PCT/IB2011/054057
§ 371 (c)(1),
(2), (4) Date: Mar. 6, 2013

(87) PCT Pub. No.: WO2012/038867
PCT Pub. Date: Mar. 29, 2012

(65) Prior Publication Data
US 2013/0172771 A1  Jul. 4, 2013

(30) Foreign Application Priority Data
Sep. 22, 2010  (EP) .................................... 10178223

(51) Int. Cl.
*A61B 5/18* (2006.01)
*B60N 2/00* (2006.01)
(Continued)

(52) U.S. Cl.
CPC .................. *A61B 5/18* (2013.01); *A61B 5/05* (2013.01); *A61B 5/0507* (2013.01);
(Continued)

(58) Field of Classification Search
CPC ............ B60N 2/002; B60N 2002/0268; A61B 5/0507; A61B 5/0205; B60R 21/01536; G01S 15/08
See application file for complete search history.

(56) References Cited

U.S. PATENT DOCUMENTS 6,050,950 A * 4/2000 Mohler .................... A61B 7/04
600/485
7,196,629 B2 * 3/2007 Ruoss et al. ............... 340/573.1
(Continued)

FOREIGN PATENT DOCUMENTS

DE  102004016191 A1  8/2005
DE  102005020847 A1  9/2006
(Continued)

*Primary Examiner* — Jacqueline Cheng
*Assistant Examiner* — Michael A Catina

(57) ABSTRACT

The invention relates to a method and device for identifying a subject in a sensor based monitoring system. This method comprises an acquisition step wherein sensors of a sensor array acquire subject related sensor signals, a pattern extraction step wherein a signal pattern is derived from the sensor signals acquired in the preceding acquisition step, and an identification step wherein the signal pattern derived in the preceding pattern extraction step is compared to predetermined signal patterns, each predetermined signal pattern being related to a subject profile, to identify a subject profile whose predetermined signal pattern related thereto matches the derived signal pattern.

15 Claims, 5 Drawing Sheets

(51) Int. Cl.

| | |
|---|---|
| *A61B 5/08* | (2006.01) |
| *G07C 5/00* | (2006.01) |
| *B60R 25/10* | (2013.01) |
| *A61B 5/00* | (2006.01) |
| *A61B 5/05* | (2021.01) |
| *B60K 25/00* | (2006.01) |
| *B60K 28/02* | (2006.01) |
| *B60R 21/015* | (2006.01) |
| *G07C 9/37* | (2020.01) |
| *A61B 5/0507* | (2021.01) |
| *A61B 5/113* | (2006.01) |
| *G01S 13/88* | (2006.01) |

(52) U.S. Cl.
CPC .......... *A61B 5/0816* (2013.01); *A61B 5/1135* (2013.01); *A61B 5/6891* (2013.01); *A61B 5/6893* (2013.01); *A61B 5/7246* (2013.01); *B60K 25/00* (2013.01); *B60K 28/02* (2013.01); *B60N 2/002* (2013.01); *B60R 21/0154* (2014.10); *B60R 25/1004* (2013.01); *G01S 13/88* (2013.01); *G07C 5/008* (2013.01); *G07C 9/37* (2020.01)

(56) References Cited

U.S. PATENT DOCUMENTS

| | | | |
|---|---|---|---|
| 2005/0267377 A1* | 12/2005 | Marossero et al. | 600/511 |
| 2007/0096446 A1* | 5/2007 | Breed | B60R 21/2338 280/735 |
| 2008/0001846 A1* | 1/2008 | Hofbeck | B60R 21/01536 343/893 |
| 2008/0221467 A1* | 9/2008 | Papyan et al. | 600/529 |
| 2008/0294019 A1* | 11/2008 | Tran | A61B 5/0006 600/301 |
| 2009/0076341 A1* | 3/2009 | James | A61B 5/0002 600/301 |
| 2009/0076405 A1* | 3/2009 | Amurthur et al. | 600/529 |
| 2010/0026479 A1* | 2/2010 | Tran | A61B 5/0006 340/501 |
| 2010/0234741 A1* | 9/2010 | Lee et al. | 600/484 |
| 2011/0125039 A1 | 5/2011 | Thijs et al. | |
| 2013/0172770 A1 | 7/2013 | Muehlsteff | |

FOREIGN PATENT DOCUMENTS

| | | | | |
|---|---|---|---|---|
| WO | WO 2009044230 A1 * | 4/2009 | | A61B 5/0402 |
| WO | 2010004496 A1 | 1/2010 | | |

* cited by examiner

METHOD AND DEVICE FOR IDENTIFYING A SUBJECT IN A SENSOR BASED MONITORING SYSTEM

FIELD OF THE INVENTION

The invention relates to the field of identifying subjects in a sensor based monitoring system comprising an array of sensors arranged for monitoring a subject, for example, a passenger in a car.

BACKGROUND OF THE INVENTION

Sensor based monitoring systems are used in various applications for monitoring physiological functions or movements of a subject. For example, such monitoring systems are used to detect the respiration effort of a human being, in order to evaluate its relaxation status. By detecting the movements of the thorax it is possible to monitor the breathing rhythm of the subject. One important application for such sensor based monitoring systems is a health check of basic vital signs of passengers e.g. after an accident. Another application is a biofeedback system based on guided breathing exercises that is provided to assist a subject to fall asleep. However, these are only selected applications that demand a monitoring of the respiration activity of a subject.

One measuring principle to monitor the respiration effort is inductive thoracic plethysmography, where a band is placed around the subject's thorax and monitors the change of the cross-sectional area of the thorax due to breathing. Although such a so-called Respiband is commonly used in medical application, however, it is not acceptable in consumer product applications, like the above mentioned biofeedback systems or driver monitoring systems in a vehicle, since the attachment of the band is inconvenient, cumbersome and not acceptable for the common user. For this reason contactless methods are preferred. Sensor based monitoring systems exist that comprise an array of contactless sensors such as radar sensors based on the Doppler Radar principle. Each of these sensors is able to detect a change of a distance of an object from the sensor. Due to their operation principle Doppler Radar sensors can be used for detecting a breathing related thorax motion as well as information related to the subject's activities. The radar sensors can be integrated in furniture such as beds, chairs etc. or in equipment in cars such as a car seat or the steering wheel. For example, for the above mentioned application of early detection of a driver's drowsiness, an array of Doppler Radar sensors can be integrated into the backrest of the driver's seat.

One problem in such applications is that signals acquired from such integrated radar sensors show a strong sensitivity with respect to characteristics of the subject such as BMI, general body size, cross section of the thorax and so on. Moreover, because the area of breathing motion is different for subjects of different size, it is desired to use only several sensors of the array to detect the breathing activity and to limit the radiant power emitted by the radar sensors as far as possible. Generally it can be stated that it is preferable to adjust and to optimize the signal acquisition by the sensors as well as the following signal analysis with respect to subject specific breathing patterns. However, with a given sensor array and signal processing methods, no possibility exists to adapt the system to an individual user.

SUMMARY OF THE INVENTION

It is therefore an object of the invention to provide a method for identifying a subject in a sensor based monitoring system that allows a clear and distinguished identification of a user so that an adaption and configuration of the systems for a following monitoring process is possible.

It is another object to provide a corresponding identification device for identifying a subject in a sensor based monitoring system.

These objects are achieved by a method according to claim 1, as well as by an identification device according to claim 12.

According to the method of the present invention, sensors of the sensor array acquire subject related sensor signals in an acquisition step that can be initiated when a subject approaches the sensor array. From the acquired sensor signals, a signal pattern is derived. That is, characteristic features of the signal in the time domain, frequency domain and/or time frequency domain are extracted by standard signal processing techniques. In the following description, the term "signal pattern" shall describe a set of such signal characteristics that is sufficient to characterize the signals acquired from one individual subject.

In a following identification step, the signal pattern derived in the preceding pattern extraction step is compared to predetermined signal patterns that can be stored in a respective storing means. Each predetermined (stored) signal pattern is related to a subject profile, referring to one subject's identity. Each subject profile may be related to a configuration of the monitoring system that fits the characteristics of the subject, for example, the number and arrangement of sensors within the array to be used when monitoring the subject, the radiant power to be emitted by the sensors, subject specific parameters for signal processing algorithms, and so on. According to the present invention, a subject profile is identified in case a predetermined signal pattern related thereto matches the signal pattern presently derived from the present subject.

The invention is based on the finding that each subject can be identified by certain characteristics of the signals acquired by the sensors, i.e. a characteristic signal pattern. A signal pattern presently derived can be used to identify the subject by comparing the present signal pattern with pre-stored signal patterns corresponding to known subjects, so that the system can be configured on the basis of the identified subject profile automatically.

According to a preferred embodiment of the present invention, this method further comprises a configuration step following the identification step, wherein the array is configured for a subsequent monitoring step in which the subject is monitored, said array being configured according to the identified subject profile. During monitoring only one sensor of the array could used for sensing the thorax motion.

Preferably the configuration of the array in the configuration step comprises the determination of a subset of sensors comprised in the array to be used in the monitoring step.

According to another preferred embodiment, wherein radar based sensors are used in the monitoring step, the configuration of the array in the configuration step comprises the determination of the radiant power to be omitted by the radar based sensors in the monitoring step.

According to another preferred embodiment, the monitoring step comprises a signal analysis using subject related parameters, said configuration step comprising the configuration of these parameters according to the identified subject profile.

According to another preferred embodiment, the method according to the present invention further comprises an approach detection step wherein sensors detect whether a subject approaches the sensors and initiate the acquisition step in case of detection that a subject approaches the sensors.

This approach detection step is provided to start the acquisition process automatically when a subject is present at the array of sensors, so that the identification process can be performed without any further input activity by the user.

Preferably the monitoring step is terminated when the sensors detect that the subject has moved away from the sensors. Thus, similar to the starting procedure, monitoring the subject is automatically stopped in this case when the subject has moved away.

According to another preferred embodiment, acceleration sensors are used in the acquisition step and/or in the monitoring step.

According to another preferred embodiment, the method according to the present invention further comprises a learning step wherein sensors of the sensor array acquire subject related sensor signals, a signal pattern is derived from the sensor signals acquired, and the derived signal pattern is stored in a data base as a predetermined signal pattern being related to a subject profile.

This learning steps serves to add another subject profile related to a corresponding signal pattern to the set of subject profiles already stored in the system. For example, the learning step can be initiated automatically when the system concludes that the present subject is not known to the system, i.e. no matching subject profile exists. In this case the signals are acquired from the sensors, a signal pattern is derived and is stored in the data base.

Preferably the learning step is initiated when no predetermined signal pattern matches the derived signal pattern in the identification step.

According to another preferred embodiment, this method further comprises a verification step wherein the subject is requested to verify the identified subject profile, said verification step following the identification step in case a subject profile is identified whose predetermined signal pattern related thereto matches the derived signal pattern.

In this embodiment a matching subject profile is not only identified automatically but the subject is also asked to verify the identification performed in the identification step. This makes the method and system more reliable.

The present invention is further related to an identification device for identifying a subject in a sensor based monitoring system, said device comprising an array of sensors, a sensor control unit communicating with the sensors comprised within said array and being provided to receive signal data from the sensors, a signal processing unit provided to receive signal data from said sensor control unit, to derive a signal pattern from said signal data, and to compare the derived signal pattern with predetermined signal patterns, and a storage unit provided for storing predetermined signal patterns and subject profiles related thereto, said storage unit communicating with said signal processing unit.

Preferably said array comprises radar sensors and/or acceleration sensors.

According to another preferred embodiment, said array is integrated into a furniture part. Such a furniture part could be, for example, the mattress of a bed, the backrest of a chair or a seat or the like.

The present invention is further related to a vehicle, comprising an identification system as described above for identifying a driver and/or a passenger of the vehicle.

BRIEF DESCRIPTION OF THE DRAWINGS

These and other aspects of the invention will be apparent from and elucidated with reference to the embodiments described hereinafter. In the drawings.

DETAILED DESCRIPTION OF EMBODIMENTS

Figure 1:
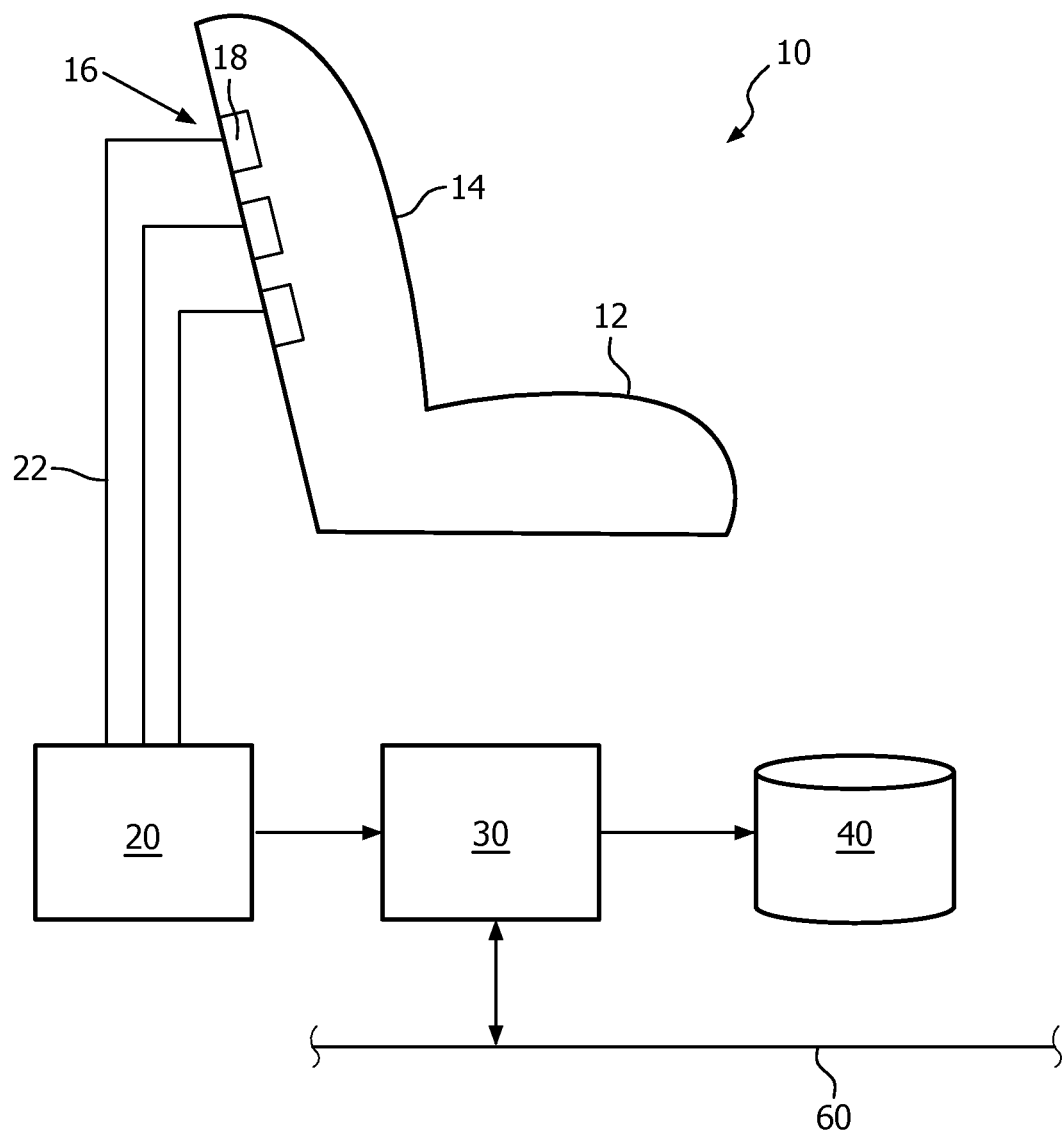
FIG. 1 is a schematic view of a sensor based monitoring system according to one embodiment of the present invention.

The sensor based monitoring system 10 shown in FIG. 1 represents a part of a vehicle comprising different seats, among others, a driver seat 12 with a backrest 14. An array 16 of different sensors 18 is integrated in the rear side of the backrest 14. These sensors 18 comprise Doppler Radar sensors to detect a motion of a subject placed on the seat 12. According to the Doppler Radar principle, the motion of the driver's thorax because of his respiration can be measured and monitored by the sensors 18. Since this motion is different at different positions, i.e. heights of the thorax, different sensors 18 can be arranged to monitor the motion as good as possible. The array 16 may further comprise acceleration sensors to detect a static and/or dynamic acceleration in order to recognize a deformation of the seat 12. In FIG. 1, only three sensors 18 are shown. However, the number of sensors can be different. What is not shown in FIG. 1 is that different sensors 18 (including Doppler Radar sensors as well as acceleration sensors) can be spread over the width of the backrest 14 so that the array 16 of sensors 18 can cover a large area at the back of the driver as the subject to be monitored.

The monitoring system 10 further comprises a sensor control unit 20 communicating with the sensors via wires or wirelessly. The sensor control unit 20 receives sensor data acquired by the sensors 18. Moreover, the sensor control unit 20 controls the activity of the sensors 18. In particular the sensor control unit 20 determines which sensors 18 of the array 16 are active during monitoring the subject. As will be explained in the following, not all sensors 18 of the array 16 may be active in the monitoring process but the number of active sensors 18 may be limited to a subset of sensors 18 comprised within the array 16. Furthermore the radiant power to be emitted by the radar based sensors 18 can be controlled by the sensor control unit 20. It is desired to configure the number of active sensors 18 and their radiant power to adapt it as good as possible to the subject's characteristics.

The monitoring system 10 further comprises a signal processing unit 30 provided to receive signal data from the sensor control unit 20. For this purpose the signal processing unit 30 communicates via wires or wirelessly with the sensor control unit 20 that transmits the sensor data received from the sensors 18 to the signal processing unit 30. The signal processing unit 30 is able to derive a signal pattern from the signal data, i.e. to analyse specific signal characteristics of these signal data in the time domain, frequency domain and/or the time frequency domain. For this analysis the signal processing unit 30 is equipped with a corresponding computing unit.

The system 10 further comprises a storage unit 40 provided for storing predetermined signal patterns and subject profiles related thereto. These subject profiles comprise subject identity data related to each stored signal pattern, and other data such as subject specific parameters for signal processing algorithms, and an optimal sensor combination of the array 16 to be used when monitoring a specific subject to which the identification information of this subject profile is related. This subject profile can be transmitted to the signal processing unit 30 for configuring the sensor array 16 via the sensor control unit 20.

To optimize the monitoring process of a specific subject, the subject in question can be identified automatically by the system. When the subject, i.e. the driver of the car takes place on the seat 12, the sensors 18 detect the approaching subject and initiate the acquisition of sensor data. These sensor data are transmitted via the sensor control unit 20 to the signal processing unit 30 that derives a signal pattern from these signal data. The signal pattern presently derived is compared to the predetermined signal patterns stored in the storage unit 40, and it is determined whether one of the pre-stored signal patterns matches the derived signal pattern. In this context the term "matching" shall denote that the derived signal pattern fits one of the predetermined signal patterns with sufficient accuracy, which means that the derived signal pattern and one of the predetermined signal patterns do not have to be exactly identical to fulfill the condition of matching.

It is noted that the signal patterns may not only be derived from the radar based sensors 18 but as well as from the acceleration sensors comprised within the array 16. The signals of acceleration sensors disposed at different positions of the seat 12 can be used to calculate a physical "deformation profile" of the seat 12, by which the subject using the seat can be identified.

In case one of the predetermined signal patterns is found to match the derived signal pattern, it is determined that the subject profile related to this predetermined signal pattern fits the subject that has taken place on the seat 12. That is, this subject has been identified by the system 10. This identification is used for a following monitoring process by transmitting the information contained in the corresponding subject profile from the storage unit 40 via the signal processing unit 30 to the sensor control unit 20 so that the array 16 of sensors 18 can be configured to correspond to the subject.

Figure 2:
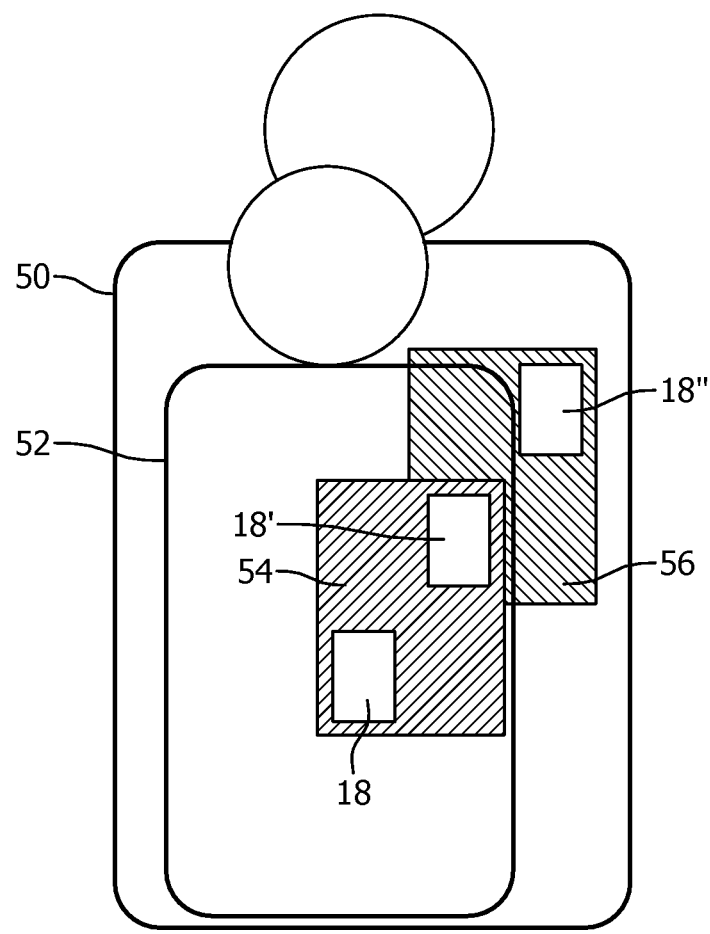
FIG. 2 is a schematic view of a sensor array of the system as shown in FIG. 1, together with two different subjects to be monitored.

One problem underlying the configuration of the sensors 18 within the array 16 is shown in FIG. 2. Two different subjects 50, 52 are shown in FIG. 2, namely a subject 50 with a smaller thorax and a larger subject 52 with a larger thorax. The breathing area, i.e. the area that performs a breathing motion during respiration of the subjects 50, 52 is different in both cases. Three sensors 18, 18', 18" are also shown in FIG. 2. For the smaller subject 50, only the lower left sensor 18 and the center sensor 18' are located within the area 54 with breathing motion, wherein the area 56 for breathing motion for the larger subject 52 comprises the center sensor 18' and the upper right sensor 18". This means that an optimal sensor configuration for the smaller subject 50 would comprise only the sensors 18 and 18', while the optimal configuration for the larger subject 52 is different and comprises the sensors 18' and 18". By the system 10 according to the present invention, each subject 50 or 52 is automatically identified and related to a corresponding subject profile that comprises the optimal sensor configuration within the array 16.

It is noted that the identification of the subject 50, 52 can also be used to control other settings of the car that comprises the monitoring system 10 to adapt it to the subject 50, 52 presently using the car. For this reason the signal processing unit 30 can be connected to the CAN Bus 60 of the car to provide the identity information to other systems and devices of a car. According to the subject identity information the car can be personalized in use by a specific subject 50, 52, e.g. personalized setting of the seats, steering wheel, heating, air conditioning, audio system.

The present method for identifying a subject 50, 52 in a sensor based monitoring system 10 will be explained in more detail with respect to the flow diagram shown in FIG. 3.

In a first detection step 100, the sensors 18 of the monitoring system 10 of FIG. 1 detect whether a subject 50, 52 approaches the sensors 18. The process of approaching can be easily detected by radar sensors, since radar signals provide the direction of a motion and during the process of an approaching subject 50, 52, relative high velocities are measured, compared to a breathing motion.

In case an approaching subject 50, 52 is detected, a following signal acquisition step 110 is initiated automatically. Within this acquisition step, the sensors 18 of the sensor array 16 acquire sensor signals from the subject 50, 52. With respect to FIG. 1, the sensor data are transmitted via the sensor control unit 20 to the signal processing unit 30.

After this acquisition step 110, a pattern extraction step 120 is performed wherein a signal pattern is derived from the sensor signals acquired in the preceding acquisition step 110. This means that the acquired sensor data are analyzed and features concerning the time domain, frequency domain and/or time frequency domain can be extracted from these signals. It is found that signal patterns derived from subject related sensor signals are different for different subjects 50, 52, which implies the possibility to distinguish different subjects 50, 52 with the help of information contained in the individual signal pattern related to each subject 50, 52. Metaphorically speaking, each signal pattern represents a kind of "fingerprint" for one subject 50, 52, that can be used in the following to identify this subject 50, 52.

The signal pattern derived in the pattern extraction step 120 is compared to a plurality of predetermined signal patterns in a subsequent identification step 130. As described above with reference to FIG. 1, these predetermined signal patterns are stored within the storage unit 40. Each predetermined signal pattern is related to a subject profile that describes the identity of a subject 50, 52 to which this signal pattern relates and contains other information that can be used to configure the monitoring system 10 for a process of monitoring the respective subject 50, 52. This means that each subject profile corresponds to an optimal configuration of the monitoring system 10 for monitoring the respective subject 50, 52. In view of the different breathing motion areas 54 and 56 in FIG. 2 for subjects 50 and 52 of different size, for example, this configuration may include the determination of a subset of sensors 18 comprised in the array 16 to be used in the monitoring process. Other configuration features may include the determination of the radiant power to be emitted by radar based sensors 18, or the configuration of parameters of a subsequent signal analysis according to the identified subject profile.

In the case in which a subject profile is identified whose predetermined signal pattern related thereto matches the derived signal pattern, the identification of the subject 50, 52 is completed, which means that a subject profile is found that matches the subject 50, 52 that is present on the seat 12 in front of the array 16 of sensors 18. In this case a feedback is given to the user in form of a visual signal on a display, an audio signal or the like, to inform the user about the identification result. In the following a configuration step 140 is initiated wherein the array 16 of sensors 18 is configured for a subsequent monitoring step 150 for monitoring the subject 50, 52. In the configuration step 140, the array 16 is configured according to the identified subject profile, as described above. This configuration may include the determination of a subset of sensors comprised in the array 16 to be used in the monitoring step 150, the determination of the radiant power of these sensors 18, and the parameters used in the signal analysis. It is, of course, possible to configure other parameters of the monitoring process performed in the monitoring step 150. During the monitoring step 150, the subject 50, 52 present at the seat 12 is monitored with respect to her/his breathing activity.

The monitoring step 150 is automatically terminated when the sensors 18 detect that the subject 50, 52 moves away from the sensors 18. This can easily be detected because of the high velocities of a moving subject 50, 52 leaving the seat 12, compared to relatively low velocities of the breathing motion. With the termination 160 of the process, the monitoring system 10 is turned off or set into a standby mode from which it can be started by the approach detection step 100 to begin again with the process described above with respect to FIG. 3.

When no predetermined signal pattern can be found in the identification step 130 that matches the derived signal pattern, this means that a subject 50, 52 is present that is unknown to the monitoring system 10. In this case a learning step 170 is initiated in which a signal pattern derived from sensor signals acquired from the present subject 50, 52 is related to a present subject profile and stored in the data base as additional predetermined signal pattern. This process is described in more detail with respect to FIG. 4. Additionally a feedback is given to the user inform him that the identification was not successful, and that a learning procedure will be started.

Within the learning step 170, a first acquisition step 120 is performed in which subject related sensor signals are acquired from the subject 50, 52. In this step 172 all sensors 18 of the array 16 are active. In a following pattern extraction step 174, characteristic features of the signals acquired in the acquisition step 172 are extracted from these signals to result in a signal pattern related to the present subject 50, 52. In an input step 176 following the pattern extraction step 174, the user is requested to input identification data that can be related to his/her subject pattern. The input data acquired in the input step 176 are stored together with subject specific features of the data signal in the database.

Moreover, on the basis of the acquired signal data (and signal pattern), parameters for a subject specific data analysis are calculated in a calculating step 180 that may follow the input step 176. The resulting calculated parameters are also stored in the data basis in a further storing step 190. From the acquired signal data and signal patterns it can be also derived which sensor arrangement should be chosen to reliably detect breathing patterns for the particular subject 50, 52. This configuration can be performed in a further sensor configuration step 200. An optimal sensor combination derived from this sensor configuration step 200 can be stored in the database in another storing step 210.

As a result, another predetermined signal pattern is stored in the database together with a related subject profile that contains information for an optimal monitoring of the respective subject, this information comprising an ideal sensor combination for measurement and subject specific features to be used in the measurement and the subsequent data analysis.

Figure 3:
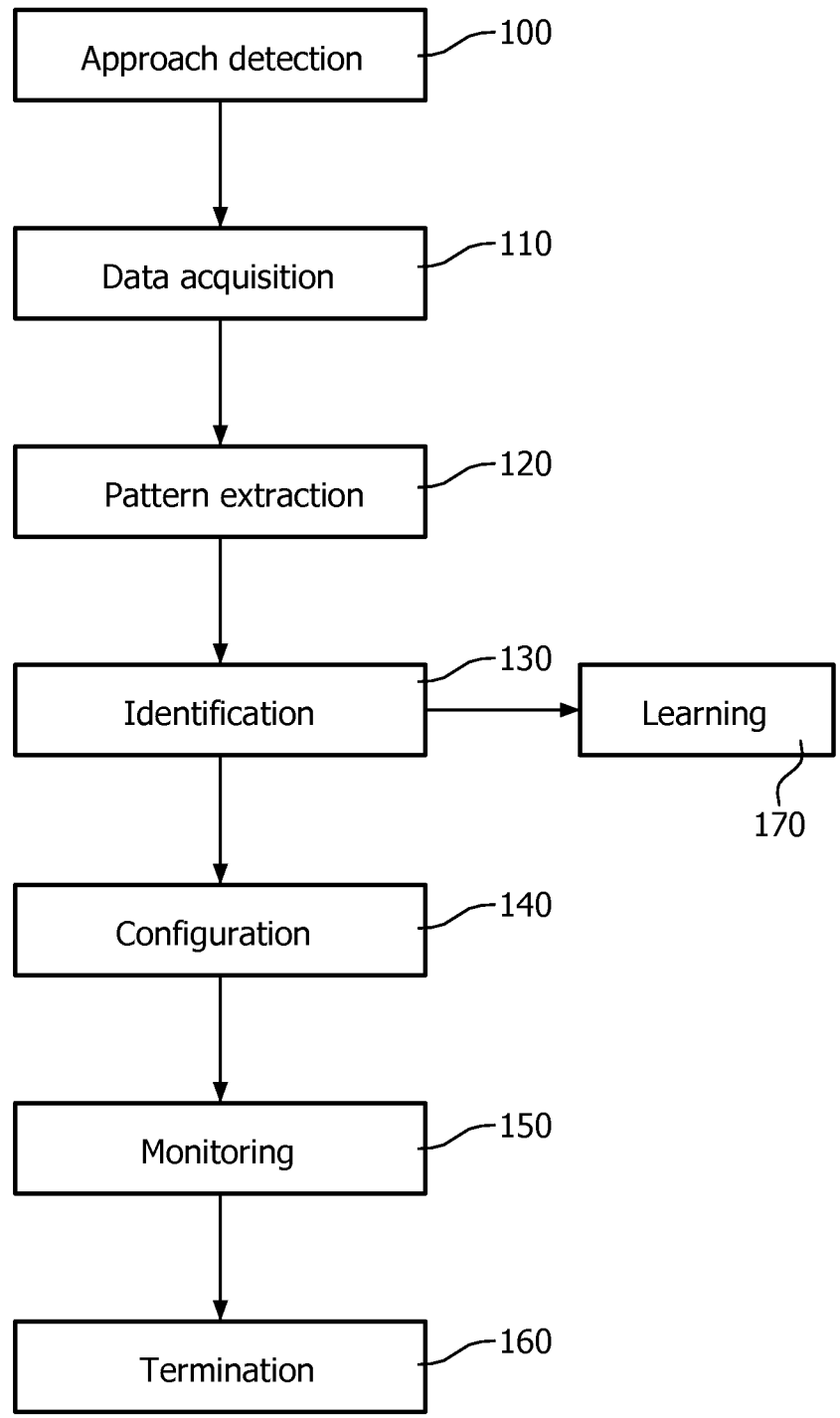
FIG. 3 is a flow diagram showing one embodiment of the method according to the present invention.
Figure 5:
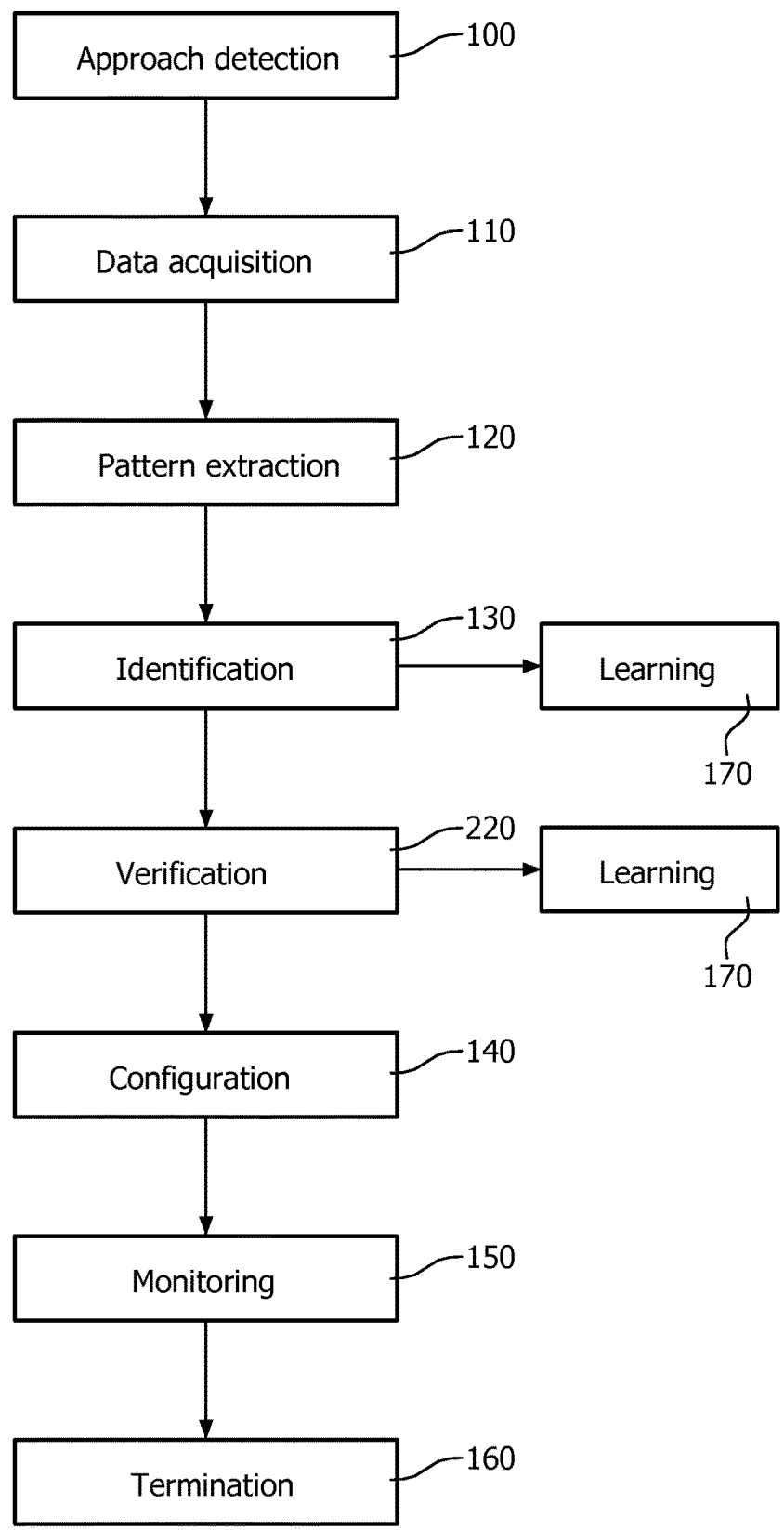
FIG. 5 is a flow diagram showing another embodiment of the identification method according to the present invention.

FIG. 5 shows another embodiment of the method for identifying a subject in a sensor based monitoring system 10 that is very similar to that described with respect to FIG. 3. It also comprises an approach detection step 100, an acquisition step 110, a pattern extraction step 120, an identification step 130, a configuration step 140, a monitoring step 150, a termination step 160 as well as a learning step 170. However, this method requests a verification by the subject to confirm the automatic identification performed in the identification step 130.

For this purpose a verification step 220 is introduced between the identification step 130 and the configuration step 140. In case the subject has been identified automatically by the system 10 in the identification step 130, i.e. a matching predetermined signal pattern is found that fits the signal pattern actually derived in the pattern extraction step 120 from the signal data acquired in the data acquisition step 110, the subject is informed accordingly by a respective signal and requested to verify the identified subject profile in a verification step 220. It is then determined whether the user input corresponds to the identified subject profile, meaning that the subject has verified his/her identity correctly. Only in case the result of this determination is positive, the verification is determined to be successful, and the configuration step 140 is performed as described with respect to FIG. 3.

Figure 4:
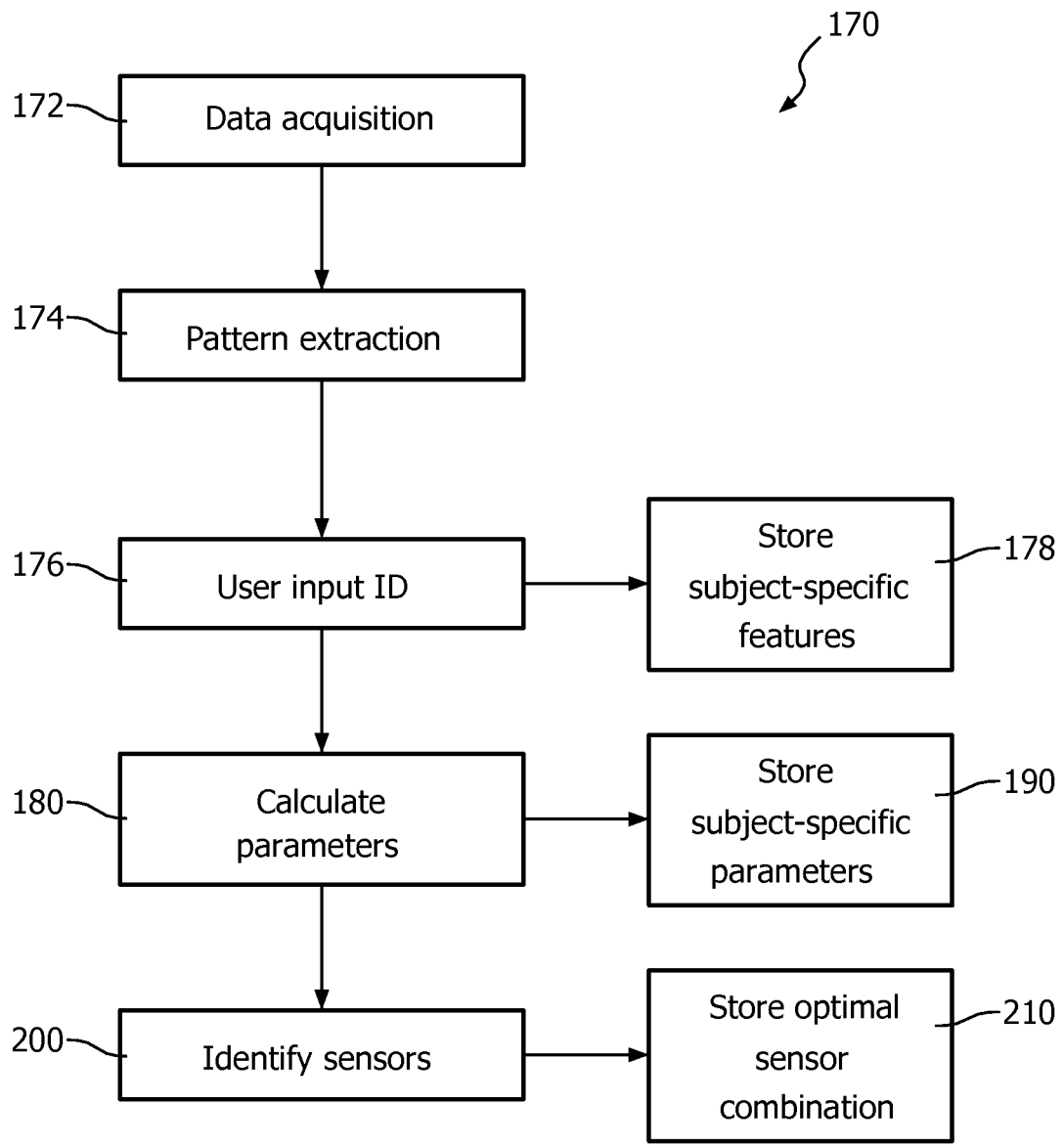
FIG. 4 is a flow diagram demonstrating details of the learning step of the method according to FIG. 3.

In case the verification result is negative, a respective information is output to the subject, and a learning step 170 is initiated automatically to determine a new signal pattern and a corresponding subject profile to be stored in the database, as described in detail with respect to FIG. 4.

The method described above with reference to FIG. 5 determines the present subject 50, 52 more reliably because the user has to verify the identity that is automatically determined in the identification step 130. If the determined identity is not confirmed by the user, a new learning process is initiated in the learning step 170.

It is noted that the method described above is not only applicable in vehicle systems to monitor the subjects breathing activity or to install subject specific preferences of the vehicle but can also be used in other systems such as biofeedback systems based on guided breathing exercises, or any other systems where the monitoring of the breathing activity of a subject is performed. Further, the method and identification system as described above could be used for a chair in a living room. Thereby a differentiation of persons could be achieved. Thus, a reliable monitoring of the thorax motion of different people is possible, since the sensor array will configured based on the identification. The identification could be further used to personalized configure devices, like TV set, Hifi system, home cinema or lighting systems.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method, comprising processor circuitry in a sensor-based monitoring system:
    acquiring from an array of sensors a plurality of subject-related sensor signals which are related to a particular subject to be identified, wherein the array of sensors includes a plurality of Doppler radar sensors,
        wherein each of the Doppler radar sensors is configured to detect a change of a distance of an object from the Doppler radar sensor,
        wherein the subject-related sensor signals are representative of a motion of a thorax of the particular subject to be identified, due to respiration by the particular subject to be identified;
    deriving from the subject-related sensor signals a signal pattern for the particular subject to be identified;
    comparing the derived signal pattern for the particular subject to be identified to a plurality of previously stored predetermined signal patterns,
        wherein each previously stored predetermined signal pattern has a corresponding previously stored subject profile stored in association with the previously stored predetermined signal pattern,
        wherein each previously stored subject profile relates to a unique configuration of the sensor-based monitoring system based on specific signal processing parameters and sensor array configuration data that fits the characteristics of a previously identified subject, and
        wherein each previously stored predetermined signal pattern is previously stored prior to acquiring the subject-related sensor signals related to the particular subject to be identified; and
    when a particular predetermined signal pattern, corresponding to a particular subject profile, matches the derived signal pattern based on the comparison:
        identifying the particular subject profile, and
        configuring the array for a subsequent monitoring of the particular subject, based on the identified particular subject profile,
    wherein configuring the array of sensors comprises determining a sub-set of sensors for monitoring the particular subject, among the sensors in the array of sensors.

2. The method of claim 1, wherein said configuring the array further comprises determining the radiant power to be emitted by the Doppler radar sensors, in the subsequent monitoring.

3. The method of claim 1, wherein:
    said subsequent monitoring comprises performing a signal analysis using subject-related parameters, and
    wherein said configuring the array comprises configuring the subject-related parameters according to the identified particular subject profile.

4. The method of claim 1, further comprising:
    at least some of the sensors of the array of sensors detecting whether said particular subject to be identified approaches the at least some sensors; and
    initiating the acquiring in case of detection that the particular subject to be identified approaches the at least some sensors.

5. The method of claim 4, wherein said subsequent monitoring is terminated when the at least some sensors detect that the particular subject to be identified has moved away from the at least some sensors.

6. The method according to claim 1, wherein acceleration sensors are used in at least one of the acquiring and the subsequent monitoring.

7. The method according to claim 1, further comprising:
    storing said derived signal pattern from the subject-related sensor signals acquired from the particular subject to be identified in a database as a new predetermined signal pattern related to a new subject profile for the particular subject to be identified.

8. The method of claim 7, further comprising initiating the storing when, based on the comparing, no predetermined signal pattern matches the derived signal pattern.

9. The method of claim 1, further comprising:
    requesting the particular user to verify the identified particular subject profile when the particular predetermined signal pattern matches the derived signal pattern based on the comparison, and the particular subject profile is identified.

10. The method of claim 1,
    wherein configuring the array for the subsequent monitoring of the particular-subject comprises selecting at least one of: a number and arrangement of the sensors within the array to be used when monitoring the particular subject, a radiant power to be emitted by the sensors when monitoring the particular subject, and subject specific parameters for signal processing,
    wherein the configuring is based on the identified particular subject profile.

11. A system, comprising:
    an array of sensors including a plurality of Doppler radar sensors and a plurality of acceleration sensors,
        wherein the array of sensors is integrated into a backrest of a seat, and
        wherein each of the Doppler radar sensors is configured to detect a change of a distance of an object from the Doppler radar sensor;
    a sensor control circuit configured to:
        acquire, from the array of sensors, subject-related sensor signals which are related to a particular subject to be identified, and
        output signal data, wherein the signal data includes first signal data, acquired from the Doppler radar sensors,
            wherein the first signal data is representative of a motion of a thorax of the particular subject to be identified, due to respiration by the particular subject to be identified, and
            wherein the signal data includes second signal data, acquired from the acceleration sensors,
            wherein the second signal data is representative of a deformation of the seat by the particular subject to be identified; and
    a signal processing circuit configured to:
        receive the signal data from the sensor control circuit,
        derive, from the acquired subject-related sensor signals, a signal pattern for the particular subject to be identified;
        compare the derived signal pattern for the particular subject to be identified to a plurality of previously stored predetermined signal patterns,
            wherein each previously stored predetermined signal pattern has a corresponding previously stored subject profile stored in association with the previously stored predetermined signal pattern,
            wherein each previously stored subject profile relates to a unique configuration of the system based on specific signal processing parameters and sensor array configuration data that fits the characteristics of a previously identified subject,
            wherein each previously stored predetermined signal pattern is previously stored prior to acquiring the subject-related sensor signals related to the particular subject to be identified; and when a particular predetermined signal pattern, corresponding to a particular subject profile, matches the derived signal pattern based on the comparison:
identify the particular subject profile, and
configure the array for a subsequent monitoring of the particular subject, based on the identified particular subject profile, wherein configuring the array of sensors comprises determining a sub-set of sensors for monitoring the particular subject, among the sensors in the array of sensors.

12. The system of claim 11, wherein the derived signal pattern, produced from the acceleration sensors, includes a deformation profile of the seat, caused by the particular subject to be identified, by which the control circuitry can identify the particular subject to be identified.

13. The system of claim 11,
wherein configuring the array for the subsequent monitoring of the particular-subject, comprises selecting at least one of: a number and arrangement of the sensors within the array to be used when monitoring the particular subject, a radiant power to be emitted by the sensors when monitoring the particular subject, and subject specific parameters for signal processing,
wherein the configuring is based on the identified particular subject profile.

14. A system, comprising:
an array of sensors including a plurality of Doppler radar sensors, wherein each of the Doppler radar sensors is configured to detect a change of a distance of an object from the Doppler radar sensor;
a sensor control circuit communicating with the array of sensors and configured to:
acquire, from the array of sensors, subject-related sensor signals which are related to a particular subject to be identified, and
output signal data, wherein the signal data is representative of a motion of a thorax of the particular subject to be identified, due to respiration by the particular subject to be identified; and
a signal processing circuit configured to:
receive the signal data from the sensor control circuit,
derive, from the received signal data, a signal pattern for the particular subject to be identified,
compare the derived signal pattern for the particular subject to be identified to a plurality of previously stored predetermined signal patterns,
wherein each previously stored predetermined signal pattern has a corresponding previously stored subject profile stored in association with the previously stored predetermined signal pattern,
wherein each previously stored subject profile relates to a unique configuration of the system based on specific signal processing parameters and sensor array configuration data that fits the characteristics of a previously identified subject,
wherein each previously stored predetermined signal pattern is previously stored prior to acquiring the subject-related sensor signals related to the particular subject to be identified, and
when a particular predetermined signal pattern, corresponding to a particular subject profile, matches the derived signal pattern based on the comparison:
identify the particular subject profile, and
configure the array for a subsequent monitoring of the particular subject, based on the identified particular subject profile,
wherein configuring the array of sensors comprises determining a sub-set of sensors for monitoring the particular subject, among the sensors in the array of sensors.

15. The system of claim 14, wherein the array is integrated into a furniture part.

* * * * *